United States Patent

Lauer et al.

Patent Number: 4,969,950
Date of Patent: Nov. 13, 1990

[54] TRIAZOLE COMPOUNDS AND METHODS FOR REGULATING PLANT GROWTH

[75] Inventors: Manfred Lauer, Ludwigshafen; Hubert Sauter, Mannheim; Karl Roeser, Hirschberg; Johann Jung, Limburgerhof; Wilhelm Rademacher, Limburgerhof; Wolfgang Will, Kirchheim, all of Fed. Rep. of Germany

[73] Assignee: BASF Aktiengesellschaft, Ludwigshafen, Fed. Rep. of Germany

[21] Appl. No.: 195,132

[22] Filed: May 17, 1988

[30] Foreign Application Priority Data

May 20, 1987 [DE] Fed. Rep. of Germany ....... 3716847
Mar. 4, 1988 [DE] Fed. Rep. of Germany ....... 3807041

[51] Int. Cl.$^5$ ............... A01N 43/653; C07D 249/08; C07D 295/00; C07D 401/02
[52] U.S. Cl. ..................... 71/92; 544/109; 546/210; 548/267.4
[58] Field of Search ............... 548/262, 267.4; 71/92; 544/109; 546/199, 210

[56] References Cited

U.S. PATENT DOCUMENTS

| | | | |
|---|---|---|---|
| 4,414,210 | 11/1983 | Miller et al. | 424/245 |
| 4,605,747 | 8/1986 | Balasubramanyan et al. | 548/262 |
| 4,614,534 | 9/1986 | Stetter et al. | 71/92 |
| 4,639,447 | 1/1987 | Roeser et al. | 514/222 |

FOREIGN PATENT DOCUMENTS 0102163 3/1984 European Pat. Off. .

OTHER PUBLICATIONS

Solomons, T. W. Graham, *Organic Chem.*, 2nd ed., John Wiley and sons, N.Y., (1980), pp. 722–723.

*Primary Examiner*—Richard L. Raymond
*Assistant Examiner*—Peter G. Sullivan
*Attorney, Agent, or Firm*—Oblon, Spivak, McClelland, Maier & Neustadt

[57] ABSTRACT

Triazole compounds of the formulae Ia and Ib

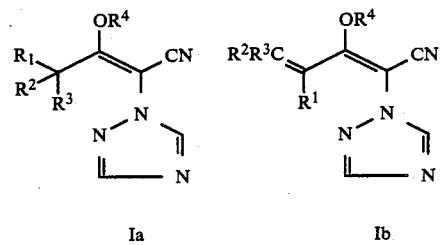

where
$R^1$ is hydrogen or cyclopropyl, or is $C_1$–$C_4$-alkyl, $C_2$–$C_4$-alkenyl or $C_2$–$C_4$-alkynyl, each of which is unsubstituted or substituted by methyl, ethyl, ethenyl, ethynyl, hydroxyl, fluorine, chlorine, bromine or $C_1$–$C_4$-alkoxy, or is $C_1$–$C_4$-alkoxy, $C_2$–$C_4$-alkenyloxy or $C_2$–$C_4$-alkynyloxy, $R^2$ and $R^3$ independently of one another are each hydrogen, straight-chain or branched $C_1$–$C_3$-alkyl, and $R^2$ and $R^3$ together may furthermore form a carbocyclic ring which has up to six members in each ring system and may possess bridge members, with the proviso that, in formula Ia, two or more of the radicals $R^1$–$R^3$ are not hydrogen, and is hydrogen, an acyl radical CO–$R^5$ or a sulfonyl radical $SO_2R^5$, $R^5$ being straight-chain or branched $C_1$–$C_8$-alkyl or unsubstituted or substituted phenyl, or is a metal cation or ammonium, are used as plant growth regulators.

9 Claims, No Drawings

TRIAZOLE COMPOUNDS AND METHODS FOR REGULATING PLANT GROWTH

The present invention relates to triazole compounds, agents which contain these triazole compounds, processes for their preparation and methods for regulating plant growth with these triazole compounds.

It is known that certain triazole compounds which are similar to the novel compounds may be suitable intermediates for the preparation of herbicides (German Laid-Open application DOS No. 3,423,101).

It is also known that 2-chloroethyltrimethylammonium chloride (J. Biol. Chem. 235 (1960), 475) has plant growth-regulating properties in cereals and other crops. It is furthermore known that triazole-substituted alcohols (German Laid-Open applications DOS Nos. 2,737,489 and 2,407,143) influence plant growth.

When the known plant growth regulators are used, the effect is often unsatisfactory, especially at low application rates and concentrations.

It is an object of the present invention to provide novel compounds which are capable of effectively regulating plant growth, in particular at low application rates.

We have found that this object is achieved and that, surprisingly, triazoles of the formulae Ia and Ib

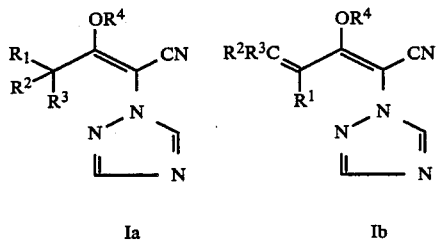

Ia                Ib where $R^1$ is hydrogen or cyclopropyl or is $C_1$–$C_4$-alkyl, $C_2$–$C_4$-alkeny, or $C_2$–$C_4$-alkynyl, each of which is unsubstituted or substituted by methyl, ethyl, ethenyl, ethynyl, hydroxyl, fluorine, chlorine, bromine or $C_1$–$C_4$-alkoxy, or is furthermore $C_1$–$C_4$-alkoxy, $C_2$–$C_4$-alkenyloxy or $C_2$–$C_4$-alkinyloxy, $R^2$ and $R^3$ independently of one another are each hydrogen or straight-chain or branched $C_1$–$C_3$-alkyl, and $R^2$ and $R^3$ together may form a carbocyclic ring which has up to six members in each ring system and may possess bridge members, with the proviso that, in formula Ia, two or more of the radicals $R^1$–$R^3$ are not hydrogen, and $R^4$ is hydrogen, an acyl radical CO—$R^5$ or a sulfonyl radical $SO_2$—$R^5$, $R^5$ in each case being straight-chain or branched $C_1$–$C_8$-alkyl or unsubstituted or substituted phenyl, or is a metal cation or ammonium, have a superior action to the agents described in, for example, German Laid-Open applications DOS Nos. 2,737,489 and 2,407,143 and to other compounds which have been used to date.

$C_1$–$C_4$-Alkyl or $C_2$–$C_4$-alkynyl in the definition of $R^1$ is, for example, methyl, ethyl, propyl, butyl, ethynyl, prop-2-ynyl, prop-1-ynyl, but-1-ynyl, but-2-ynyl or but-3-ynyl. $C_1$–$C_4$-alkoxy is, for example, methoxy, ethoxy, propoxy, isopropoxy, butoxy, isobutoxy, sec-butoxy or tert-butoxy. $C_2$–$C_4$-alkenyloxy or alkynyloxy is, for example, ethenyl-, ethynyl-, prop-2-enyl-, prop-2-ynyl-, prop-1-enyl-, but-1-enyl-, but-1-ynyl-, but-2-enyl-, but-3-enyl- or but-3-ynyloxy.

In the definition of $R^2$ and $R^3$, $C_1$–$C_3$-alkyl is, for example, methyl, ethyl, propyl or isopropyl. $R^2$ and $R^3$ may further be bonded to one another to form a carbocyclic system, for example a ring of 3 to 6 carbon atoms, such as cyclopropyl, cyclobutyl, cyclopentyl or cyclohexyl. This ring may additionally be bridged by, for example, a $C_1$- or $C_2$-bridge so that a bicyclic radical, such as bicyclo[2.2.1] heptyl (norbornyl), bicyclo[2.2.2]octyl or bicyclo[2.1.1] hexyl, is formed.

Examples of the group $CR^1R^2R^3$ are 2-propyl, tert-butyl, 1-methylpropyl, 1,1-dimethylpropyl, 1,1-dimethylbutyl, 1-methyl-1-ethylpropyl, 1-ethylpropyl, 1-ethylpropen-1-yl, cyclopentyl, cyclohexyl, 1-methyl-1-methoxyethyl and 1-methyl-1-ethoxyethyl. Preferred compounds are those in which $R^1$ and $R^2$ are each ethyl and $R^3$ is hydrogen or methyl.

$R^4$ is a cation of an alkali or alkaline earth metal, e.g. sodium, potassium or magnesium, ammonium including the cations of organic amines, such as methylamine, dimethylamine, trimethylamine, diisopropylamine, N-methyldiisopropylamine, N-ethyldiisopropylamine, dicyclohexylamine, piperidine, N-methylpiperidine, the N,N-dimethylpiperidinium ion, N-methyl-N-hexylamine or morpholine, or an acyl radical CO—$R^5$ or a sulfonyl radical $SO_2R^5$.

In the acyl radical CO—$R^5$ or sulfonyl radical $SO_2R^5$, $R^5$ is $C_1$- to $C_8$-alkyl, such as methyl, ethyl, propyl, isopropyl, butyl, isobutyl, sec-butyl, tert-butyl, pentyl, isopentyl, hexyl, isohexyl, heptyl, isoheptyl, octyl or isooctyl, or unsubstituted or substituted phenyl. Examples of substituents on the phenyl ring are halogen, such as fluorine, chlorine, bromine or iodine, $C_1$–$C_4$-alkyl, $C_2$–$C_4$-alkenyl, $C_1$–$C_4$-alkoxy and cyano. The phenyl ring may carry from 1 to 5, in particular from 1 to 3, inert substituents.

Triazole compounds of the formula I in which $R^1$, $R^2$ and $R^3$ have the abovementioned meanings and $R^4$ is hydrogen are prepared by acylation of triazolylacetonitrile with an acylating agent of the formula $R^1R^2R^3CCOX$, where $R^1$–$R^3$ have the abovementioned meanings and X is chlorine, bromine or iodine. For economic reasons, the chloride is preferred.

Examples of suitable acylating agents are propionyl chloride, butyryl chloride, isobutyryl chloride, 2-methylbutyryl chloride, pivaloyl chloride, 2,2-dimethylbutyryl chloride, 2-ethylbutyryl chloride, 2,2-methyl-2-ethylbutyryl chloride, 2-methylvaleroyl chloride, 2,2-dimethylvaleroyl chloride, 2-ethylvaleroyl chloride, 2-methyl-2-ethylvaleroyl chloride, 2,2-diethylvaleroyl chloride, 2-isopropylpropionyl chloride, 2-methoxypropionyl chloride, 2-methoxy-2-methylpropionyl chloride, cyclopentylcarbonyl chloride and 1-methylcyclopentylcarbonyl chloride.

The reaction is carried out in the presence or absence of a suitable diluent at from −50° to +150° C. Examples of suitable solvents are ethers, such as diethyl ether, methyl tert-butyl ether, tetrahydrofuran or dioxane, chlorohydrocarbons, such as methylene chloride, aromatic hydrocarbons, such as toluene or xylene, ketones, such as acetone, and alcohols, such as tert-butanol, as well as dimethylformamide and dimethyl sulfoxide.

Examples of suitable bases or acid acceptors are hydroxides of alkali and alkaline earth metals, such as sodium hydroxide, potassium hydroxide and calcium hydroxide, alcoholates of alkali and alkaline earth metals, such as sodium methylate, sodium ethylate, calcium methanolate or potassium tert-butylate, alkali metal or alkaline earth metal hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, and aromatic amines, such as pyridine or pyrrole, in stoichiometric amounts or in excess.

The compounds Ia and Ib are obtained as Z/E isomer mixtures which, in the case of the hydroxy compounds, may be in equilibrium with the corresponding keto form, exhibiting keto-enol tautomerism. The particular amounts of Z- and E-enol and the tautomeric keto compounds depend to a great extent on ambient effects, such as temperature or solvent. The present invention relates to the individual isomers and mixtures of these isomers.

Triazole compounds of the formula Ia or Ib in which $R^4$ is not hydrogen but an acyl radical CO—$R^5$, where $R^5$ has the abovementioned meanings, can be obtained in a one-stage reaction, as described above for the free hydroxy compound, by acylation of triazolylacetonitrile, but in the presence of not less than two equivalents of an acyl chloride. For $R^4$=CO—$R^5$, however, it is advantageous to carry out a two-stage reaction in which the compound is prepared by acylation of the compound I where $R^4$ is H. Suitable acylating agents are the compounds described above, for example acetyl chloride, pivaloyl chloride, 2-ethylbutyryl chloride, 2-methylbutyryl chloride or benzoyl chloride.

Triazole compounds of the formula Ia or Ib in which $R^4$ is not hydrogen but a sulfonyl radical $SO_2R^5$, where $R^5$ has the abovementioned meanings, are prepared by reacting the corresponding hydroxy compound I (where $R^4$ is H) with a sulfonyl halide X—$SO_2$—$R^5$, where X is halogen, such as chlorine, bromine or iodine, and $R^5$ has the abovementioned meanings, or with a correspondingly substituted sulfonic anhydride in the presence of a base.

Suitable bases or acid acceptors are the conventional compounds stated above, such as alkali metal or alkaline earth metal compounds, for example carbonates, hydroxides or alcoholates, tertiary amines or unsubstituted or substituted pyridine. Examples are sodium carbonate, sodium hydroxide, potassium hydroxide, potassium tert-butylate, trimethylamine, triethylamine, N-methylpiperidine or pyridine. The reaction can advantageously be carried out in the presence of a catalytic amount of 4-N-N'-dimethylaminopyridine.

The base can be used in stoichiometric amounts or in excess, advantageously in an amount of from 1 to 2 moles per mole of the hydroxy compound I where $R^4$ is H.

The sulfonyl halide or sulfonic anhydride is usually used in equimolar amounts, based on the hydroxy compound. An excess or less than the stoichiometric amount, e.g. from 0.5 to 2 moles, is also possible.

The reaction is carried out in the presence or absence of a solvent at from −50 to +150° C. Examples of suitable solvents or diluents are ethers, such as tetrahydrofuran, Diethyl ether, methyl tert-butyl ether or dioxane, chlorohydrocarbons, such as methylene chloride, aromatic hydrocarbons, such as toluene or xylene, ketones, e.g. acetone, alcohols, such as tert-butanol, amides, such as dimethylformamide, and sulfoxides, such as dimethyl sulfoxide.

Triazole compounds of the formula Ia or Ib in which $R^4$ is not hydrogen but a metal cation or ammonium cation are prepared by reacting the corresponding hydroxy compound I and a suitable base in the presence or absence of a suitable diluent. Examples of suitable bases are sodium hydroxide solution, potassium hydroxide solution, dimethylamine, diethylamine, trimethylamine, triethylamine, ethanolamine, diethanolamine, triethanolamine, diisopropylamine, diisopropylethylamine, piperidine, dicyclohexylamine, N-methylpiperidine, morpholine and 2,6-dimethylmorpholine. The amount of base is not particularly critical; the base may be used in equimolar amounts or in excess, based on the hydroxy compounds, for example in an amount of from 1 to 2 moles per mole of I.

PREPARATION EXAMPLE 1

130 g (1.2 moles) of potassium tert-butylate are added a little at a time to a solution of 68 g (0.5 mole) of 2-ethylbutyryl chloride and 54 g (0.5 mole) of triazolyl acetonitrile in 500 ml of tetrahydrofuran at −20° C. The mixture is allowed to reach room temperature, stirred for a further 12 hours and evaporated down, and the residue is diluted with 1,000 ml of water. After impurities have been extracted with methyl tert-butyl ether, the aqueous phase is acidified with dilute hydrochloric acid and extracted several times with methylene chloride. The organic phase is evaporated down and the resulting 1-cyano-1-(1,2,4-triazol-1-yl)-3-ethyl-1-penten-2-ol is recrystallized from ethanol/water. Yield 73 g (71% of theory); mp. 98–103° C.

The compound obtained is listed as No. 49 in the table below.

PREPARATION EXAMPLE 2

6 g (29 mmol) of the compound 49, obtained as described above, are dissolved in pyridine and reacted with 35 ml (30 mmol) of benzoyl chloride for 5 hours at 50° C. in the presence of a catalytic amount of dimethylaminopyridine. After the mixture has been evaporated down, the reaction product is purified by chromatographing it over a column. 0.5 g (14%) of 2-benzoyl-1-cyano-1-(1,2,4-triazol-1-yl)-3-ethyl-1-pentene is obtained in the form of a Z/E isomer mixture (No. 89 in Table 1) IR: 2970, 1757, 1505, 1205, 1086 cm$^{-1}$

PREPARATION EXAMPLE 3

0.5 g of 4-N,N'-dimethylaminopyridine and then 50 g (0.25 mol) of p-toluenesulfonyl chloride are added to a suspension of 50 g (0.24 mol) of 1-cyano-1-(1,2,4-triazol-1-yl)-3-ethyl-1-penten-2-ol in 300 ml of toluene. 50 ml (0.36 mol) of triethylamine are then added dropwise. Stirring is carried out for 40 hours at room temperature, the mixture is extracted by shaking with water, the organic phase is evaporated down and the product is allowed to crystallize out. Recrystallization from ethanol gives 60 g (68%) of 2-(4-methylphenylsulfonyl)-1-cyano-1-(1,2,4-triazolyl)-3-ethyl-1-pentene in the form of a Z/E isomer mixture. Mp. 78–87° C.

$C_{17}H_{20}N_4O_3S$ calc. C 56.7 H 5.6 N 15.5 S 8.9.
found C 56.7 H 5.8 N 15.6 S 8.8.

The compound obtained is listed as No. 109 in the table below.

Where physical data are specified, the active ingredients stated by way of example in the table below were each prepared. The other compounds can be obtained from corresponding intermediates by means of the stated measures; because of this similarity, they are likely to have a comparable action.

TABLE 1

Triazole compounds of the formula $$\begin{array}{c} OR^4 \\ R^1 \\ R^2 \\ R^3 \end{array} \begin{array}{c} CN \\ N \\ N \\ N \end{array} \quad Ia$$

| No. | $R^1$ | $R^2$ | $R^3$ | $R^4$ | m.p./IR (cm$^{-1}$) |
|---|---|---|---|---|---|
| 1 | $CH_3$— | $CH_3$ | H | H | 78–80° C. |
| 2 | $C_2H_5$— | $CH_3$ | H | H | 87° C. |
| 3 | $CH_2=CH$— | $CH_3$ | H | H | |
| 4 | $CH\equiv C$— | $CH_3$ | H | H | |
| 5 | $CH_3CH_2CH_2$— | $CH_3$ | H | H | 2961, 2935, 1633, 1508 |
| 6 | $(CH_3)_2CH$— | $CH_3$ | H | H | 117° C. |
| 7 | cyclopropyl | $CH_3$ | H | H | |
| 8 | $CH_2=CH-CH_2$— | $CH_3$ | H | H | |
| 9 | $CH\equiv C-CH_2$— | $CH_3$ | H | H | |
| 10 | $CH_3CH_2CH_2CH_2$— | $CH_3$ | H | H | |
| 11 | $(CH_3)_2CHCH_2$— | $CH_3$ | H | H | |
| 12 | $CH_3CH(CH_3)CH_2$— | $CH_3$ | H | H | |
| 13 | $(CH_3)_3C$— | $CH_3$ | H | H | |
| 14 | $CH_2=CHCH_2CH_2$— | $CH_3$ | H | H | |
| 15 | $CH\equiv C-CH_2CH_2$— | $CH_3$ | H | H | |
| 16 | $HOCH_2$— | $CH_3$ | H | H | |
| 17 | $FCH_2$— | $CH_3$ | H | H | |
| 18 | $ClCH_2$— | $CH_3$ | H | H | |
| 19 | $CH_3O$— | $CH_3$ | H | H | 117–118° C. |
| 20 | $CH_3OCH_2$— | $CH_3$ | H | H | |
| 21 | $CH_3CH_2OCH_2$— | $CH_3$ | H | H | |
| 22 | $CH_2=CHCH_2OCH_2$— | $CH_3$ | H | H | |
| 23 | $CH\equiv CCH_2OCH_2$— | $CH_3$ | H | H | |
| 24 | $CH_3CH_2CH_2CH_2OCH_2$— | $CH_3$ | H | H | |
| 25 | $CH_3$— | $CH_3$ | $CH_3$ | H | 2976, 1738, 1506, 1277 |
| 26 | $C_2H_5$— | $CH_3$ | $CH_3$ | H | 2973, 1736, 1505, 1278 |
| 27 | $CH_2=CH$— | $CH_3$ | $CH_3$ | H | |
| 28 | $CH\equiv C$— | $CH_3$ | $CH_3$ | H | |
| 29 | $CH_3CH_2CH_2$— | $CH_3$ | $CH_3$ | H | 2965, 1505, 1474, 1279 |
| 30 | $(CH_3)_2CH$— | $CH_3$ | $CH_3$ | H | |
| 31 | cyclopropyl | $CH_3$ | $CH_3$ | H | |
| 32 | $CH_2=CHCH_2$— | $CH_3$ | $CH_3$ | H | |
| 33 | $CH\equiv CCH_2$— | $CH_3$ | $CH_3$ | H | |
| 34 | $CH_3CH_2CH_2CH_2$— | $CH_3$ | $CH_3$ | H | |
| 35 | $(CH_3)_2CHCH_2$— | $CH_3$ | $CH_3$ | H | |
| 36 | $CH_3CH(CH_3)CH_2$— | $CH_3$ | $CH_3$ | H | |
| 37 | $(CH_3)_3C$— | $CH_3$ | $CH_3$ | H | |
| 38 | $CH_2=CHCH_2CH_2$— | $CH_3$ | $CH_3$ | H | |
| 39 | $CH\equiv CCH_2CH_2$— | $CH_3$ | $CH_3$ | H | |
| 40 | $HOCH_2$— | $CH_3$ | $CH_3$ | H | xHCl → 171–179° C. |
| 41 | $FCH_2$— | $CH_3$ | $CH_3$ | H | |
| 42 | $ClCH_2$— | $CH_3$ | $CH_3$ | H | |
| 43 | $CH_3O$— | $CH_3$ | $CH_3$ | H | |
| 44 | $CH_3OCH_2$— | $CH_3$ | $CH_3$ | H | 2936, 1739, 1506, 1277 |
| 45 | $CH_3CH_2OCH_2$— | $CH_3$ | $CH_3$ | H | 2978, 1739, 1505, 1277, 1113 |
| 46 | $CH_2=CH-CH_2OCH_2$— | $CH_3$ | $CH_3$ | H | |
| 47 | $CH\equiv C-CH_2OCH_2$— | $CH_3$ | $CH_3$ | H | |
| 48 | $CH_3CH_2CH_2CH_2OCH_2$— | $CH_3$ | $CH_3$ | H | 2960, 1739, 1474, 1277 |
| 49 | $C_2H_5$— | $C_2H_5$ | H | H | 98–103° C. |
| 50 | $CH_2=CH$— | $C_2H_5$ | H | H | |
| 51 | $CH\equiv C$— | $C_2H_5$ | H | H | |
| 52 | $CH_3CH_2CH_2$— | $C_2H_5$ | H | H | |
| 53 | $(CH_3)_2CH$— | $C_2H_5$ | H | H | |
| 54 | $CH_2=CHCH_2$— | $C_2H_5$ | H | H | |
| 55 | $CH\equiv CCH_2$— | $C_2H_5$ | H | H | |
| 56 | $CH_3CH_2CH_2CH_2$— | $C_2H_5$ | H | H | 59–61° C. |
| 57 | $(CH_3)_2CHCH_2$— | $C_2H_5$ | H | H | |
| 58 | $CH_3CH(CH_3)CH_2$— | $C_2H_5$ | H | H | |
| 59 | $C_2H_5$— | $C_2H_5$ | $CH_3$ | H | 3112, 2969, 2207, 1520 |
| 60 | $CH_2=CH$— | $C_2H_5$ | $CH_3$ | H | |
| 61 | $CH\equiv C$— | $C_2H_5$ | $CH_3$ | H | |
| 62 | $CH_3CH_2CH_2$— | $C_2H_5$ | $CH_3$ | H | |
| 63 | $CH_3CH_2CH_2CH_2$— | $C_2H_5$ | $CH_3$ | H | |
| 64 | $C_2H_5$— | $C_2H_5$ | $C_2H_5$ | H | |
| 65 | $CH_3CH_2CH_2$— | $CH_3$ | $C_2H_5$ | H | |
| 66 | $CH_3CH_2CH_2CH_2$— | $CH_3$ | $C_2H_5$ | H | |

TABLE 1-continued

Triazole compounds of the formula

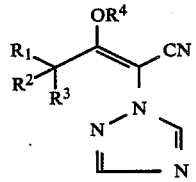

Ia

| No. | R¹ | R² | R³ | R⁴ | m.p./IR (cm⁻¹) |
|---|---|---|---|---|---|
| 67 | CH₃CH₂CH₂— | n-C₃H₇ | H | H | 88–91° C. |
| 68 | CH₃CH₂CH₂— | CH₃ | H | H | |
| 69 | CH₃CH₂CH₂— | C₂H₅ | H | H | |
| 70 | CH₃CH₂CH₂— | C₃H₇ | H | H | |
| 71 | H— | cyclopropyl | H | H | 2209, 1592, 1508, 1277 |
| 72 | CH₃— | cyclopropyl | H | H | 152–156° C. |
| 73 | H— | cyclobutyl | H | H | 2950, 1624, 1508, 1277 |
| 74 | CH₃— | cyclobutyl | H | H | |
| 75 | H | cyclopentyl | H | H | 81–82° C. |
| 76 | CH₃ | cyclopentyl | H | H | |
| 77 | H | cyclohexyl | H | H | 121–125° C. |
| 78 | CH₃ | cyclohexyl | H | H | 2935, 1504, 1277, 1134 |
| 79 | H | adamantyl | H | H | 114–117° C. |
| 80 | CH₃ | adamantyl | H | H | |
| 81 | C₂H₅ | C₂H₅ | H | COH | |
| 82 | C₂H₅ | C₂H₅ | H | COCH₃ | 2970, 1757, 1505, 1205 |
| 83 | C₂H₅ | C₂H₅ | H | COC₂H₅ | 2967, 1785, 1506, 1087 |
| 84 | C₂H₅ | C₂H₅ | H | COCH₂CH₃CH₃ | |
| 85 | C₂H₅ | C₂H₅ | H | COCH₂CH₂CH₂CH₃ | |
| 86 | C₂H₅ | C₂H₅ | H | COC(CH₃)₃ | |
| 87 | C₂H₅ | C₂H₅ | H | COCH(CH₃)CH₂CH₃ | |
| 88 | C₂H₅ | C₂H₅ | H | COCH(C₂H₅)₂ | |
| 89 | C₂H₅ | C₂H₅ | H | —CO—C₆H₅ | 2970, 1757, 1505, 1205 |
| 90 | C₂H₅ | C₂H₅ | H | —CO—C₆H₄—Cl | 1758, 1593, 1204, 1089 |
| 91 | C₂H₅ | C₂H₅ | H | —CO—C₆H₄—NO₂ | |
| 92 | C₂H₅ | C₂H₅ | H | —CO—C₆H₃(CH₃)(NO₂) | |
| 93 | C₂H₅ | C₂H₅ | H | —CO—C₆H₄—Cl (2-Cl) | 2967, 1770, 1585, 1201 |
| 94 | CH₃ | C₂H₅ | H | —CO—CH₃ | 2970, 2937, 2217, 1633 |
| 95 | CH₃ | CH₃ | CH₃ | SO₂CH₃ | 1362, 1187, 1088, 795 |
| 96 | CH₃ | CH₃ | CH₃ | SO₂—C₆H₅ | |

TABLE 1-continued
Triazole compounds of the formula Ia
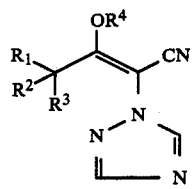
| No. | R¹ | R² | R³ | R⁴ | m.p./IR (cm⁻¹) |
|---|---|---|---|---|---|
| 97 | CH₃ | CH₃ | CH₃ | -SO₂-C₆H₄- (p) | |
| 98 | CH₃ | CH₃ | CH₃ | -SO₂-(2,4,6-trimethylphenyl) | |
| 99 | H | CH₃ | C₂H₅ | SO₃CH₃ | 60–65° C. |
| 100 | H | CH₃ | C₂H₅ | -SO₂-C₆H₅ | |
| 101 | H | CH₃ | C₂H₅ | -SO₂-C₆H₄- (p) | |
| 102 | H | CH₃ | C₂H₅ | -SO₂-(2,4,6-trimethylphenyl) | 1371, 1176, 1210, 1053 |
| 103 | H | CH₃ | i-C₃H₇ | SO₂CH₃ | |
| 104 | H | CH₃ | i-C₃H₇ | -SO₂-C₆H₅ | |
| 105 | H | CH₃ | i-C₃H₇ | -SO₂-C₆H₄- (p) | 30–40° C. |
| 106 | H | CH₃ | i-C₃H₇ | -SO₂-(2,4,6-trimethylphenyl) | |
| 107 | H | C₂H₅ | C₂H₅ | SO₂CH₃ | 1506, 1372, 1210, 1177 |
| 108 | H | C₂H₅ | C₂H₅ | -SO₂-C₆H₅ | |

TABLE 1-continued

Triazole compounds of the formula Ia

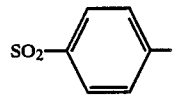

| No. | R¹ | R² | R³ | R⁴ | m.p./IR (cm$^{-1}$) |
|---|---|---|---|---|---|
| 109 | H | $C_2H_5$ | $C_2H_5$ | 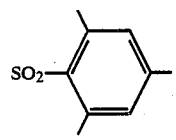 | 78–87° C. |
| 110 | H | $C_2H_5$ | $C_2H_5$ | 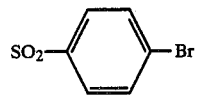 | 2968, 1054, 1370, 1175 |
| 111 | H | $C_2H_5$ | $C_2H_5$ | 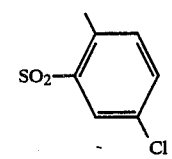 | 108–114° C. |
| 112 | H | $C_2H_5$ | $C_2H_5$ | 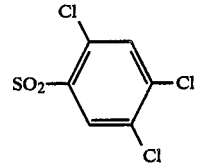 | 112–116° C. |
| 113 | H | $C_2H_5$ | $C_2H_5$ | 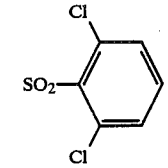 | 137–139° C. |
| 114 | H | $C_2H_5$ | $C_2H_5$ | 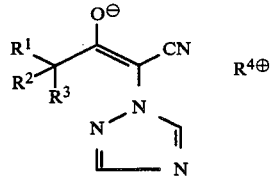 | 100–104° C. |

TABLE 2

Triazole compounds of the formula

| No. | R¹ | R² | R³ | R⁴ | m.p./IR (cm$^{-1}$) |
|---|---|---|---|---|---|
| 115 | $C_2H_5$ | $C_2H_5$ | H | $Na^{\oplus}$ | 95–100° C. |
| 116 | $C_2H_5$ | $C_2H_5$ | H | $K^{\oplus}$ | |
| 117 | $C_2H_5$ | $C_2H_5$ | H | $NH_4^{\oplus}$ | |
| 118 | $C_2H_5$ | $C_2H_5$ | H | $CH_3\overset{\oplus}{N}H_3$ | |
| 119 | $C_2H_5$ | $C_2H_5$ | H | $(CH_3)_2\overset{\oplus}{N}H_2$ | |

TABLE 2-continued

| No. | $R^1$ | $R^2$ | $R^3$ | $R^4$ | m.p./IR (cm$^{-1}$) |
|---|---|---|---|---|---|
| 120 | $C_2H_5$ | $C_2H_5$ | H | $(CH_3)_3\overset{\oplus}{N}H$ | |
| 121 | $C_2H_5$ | $C_2H_5$ | H | $(CH_4)\overset{\oplus}{N}$ | |
| 122 | $C_2H_5$ | $C_2H_5$ | H | $(C_2H_5)_2\overset{\oplus}{N}H_2$ | |
| 123 | $C_2H_5$ | $C_2H_5$ | H | $(C_2H_5)_3\overset{\oplus}{N}H$ | |
| 124 | $C_2H_5$ | $C_2H_5$ | H | $((CH_3)_2CH)\overset{\oplus}{N}H_3$ | |
| 125 | $C_2H_5$ | $C_2H_5$ | H | $((CH_3)_2CH)_2\overset{\oplus}{N}H_2$ | 2962, 2170, 1539, 1275 |
| 126 | $C_2H_5$ | $C_2H_5$ | H | $((CH_3)_2CH)_2\overset{\oplus}{N}HCH_3$ | |
| 127 | $C_2H_5$ | $C_2H_5$ | H | $((CH_3)_2CH)_2\overset{\oplus}{N}HC_2H_5$ | |
| 128 | $C_2H_5$ | $C_2H_5$ | H | cyclohexyl-$\overset{\oplus}{N}H_3$ | |
| 129 | $C_2H_5$ | $C_2H_5$ | H | $(cyclohexyl)_2$-$\overset{\oplus}{N}H_2$ | |
| 130 | $C_2H_5$ | $C_2H_5$ | H | 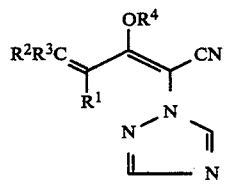 | |
| 131 | $C_2H_5$ | $C_2H_5$ | H | piperidinium (N,N-dimethyl) | |
| 132 | $C_2H_5$ | $C_2H_5$ | H | $Cl-CH_2CH_2-\overset{\oplus}{N}(CH_3)_2$ | $^1$H-NMR in CDCl$_3$ (ppm): 0.85(t); 3.2(d); 3.8(d); 4.1(t); 7.85(s); 8.55(s) |
| 133 | $C_2H_5$ | $C_2H_5$ | H | $(HOCH_2CH_2)_2\overset{\oplus}{N}H_2$ | 2961, 2175, 1537, 1457, 1403 |

$$\underset{\substack{R^1 \\ \\ N\!\!-\!\!N \\ \parallel \quad \diagdown \\ \phantom{N}\quad N}}{R^2R^3C\diagdown\!\!\underset{}{\overset{OR^4}{\overset{|}{C}}}\!\!=\!\!\underset{}{\overset{}{C}}\diagup^{CN}} \qquad \text{Ib}$$

Triazole compounds of the formula Ib

| No. | $R^1$ | $R^2$ | $R^3$ | $R^4$ | m.p. |
|---|---|---|---|---|---|
| 134 | H | H | H | H | |
| 135 | H | $CH_3$ | H | H | |
| 136 | H | $CH_3$ | $CH_3$ | H | 118° C. |
| 137 | H | $C_2H_5$ | H | H | |
| 138 | H | $C_2H_5$ | $CH_3$ | H | |
| 139 | H | $C_2H_5$ | $C_2H_5$ | H | |
| 140 | $CH_3$ | H | H | H | |
| 141 | $CH_3$ | $CH_3$ | H | H | 64–71° C. |
| 142 | $CH_3$ | $CH_3$ | $CH_3$ | H | |
| 143 | $CH_3$ | $C_2H_5$ | H | H | |
| 144 | $CH_3$ | $C_2H_5$ | $C_2H_5$ | H | |
| 145 | $CH_3$ | $C_2H_5$ | $C_2H_5$ | H | |
| 146 | $C_2H_5$ | H | H | H | |
| 147 | $C_2H_5$ | $CH_3$ | H | H | 81–88° C. |
| 148 | $C_2H_5$ | $CH_3$ | $CH_3$ | H | |
| 149 | $C_2H_5$ | $C_2H_5$ | H | H | |
| 150 | $C_2H_5$ | $C_2H_5$ | $CH_3$ | H | |
| 151 | $C_2H_5$ | $C_2H_5$ | $C_2H_5$ | H | |

The triazole derivatives of the formula I may have a variety of influences on practically all plant development stages, and may therefore be used as growth regulators. The diversity of action of growth regulators depends especially on (a) the type and variety of plant;
(b) the time applied, with reference to the development stage of the plant and the time of the year;
(c) the place and method of application (seed treatment, soil treatment, or foliage application);
(d) climatic factors, e.g., temperature, amount of precipitate, day length and light intensity;
(e) soil conditions (including fertilization);
(f) the formulation of the active ingredient; and
(g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The triazole derivatives of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients to be used in accordance with the invention may be applied not only to the seed (as a disinfectant), but also to the soil, i.e., via the roots, and to the foliage.

As a result of the good crop plant tolerance, the application rate may vary considerably. When seed is treated, active ingredient amounts of from 0.001 to 50, and preferably from 0.01 to 10, g per kg of seed are generally needed. When the soil or foliage is treated, rates of from 0.01 to 10, and preferably from 0.05 to 3, kg per hectare are generally considered to be sufficient.

The novel substances can be employed in the form of conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, benzene), chlorinated aromatics (e.g., chlorobenzenes), paraffins (e.g., crude oil fractions), alcohols (e.g., methanol, butanol), amines (e.g., ethanolamine) N,N-dimethylformamide, and water; solid carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates); and dispersants such as lignin, sulfite waste liquors and methylcellulose. It is preferred to apply the active ingredients according to the invention in aqueous solution, if desired with the addition of water-miscible organic solvents such as methanol or other lower alcohols, acetone, N,N-dimethylformamide or N-methylpyrrolidone. The fungicides generally contain from 0.1 to 95, and preferably from 0.5 to 90, wt % of active ingredient.

The formulations, or the ready-to-use preparations prepared therefrom, such as solutions, emulsions, suspensions, powders, dusts, pastes or granules, are applied in known manner, for example preemergence, postemergence, or as seed disinfectants.

Examples of formulations are given below.

I. 20 parts by weight of the compound of Example 1 is well mixed with 3 parts by weight of the sodium salt of diisobutylnaphthalene-αsulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 133 is intimately mixed with 97 parts by weight of particulate kaolin. A dust is obtained containing 3% by weight of the active ingredient.

III. 30 parts by weight of the compound of Example 110 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 20 parts of the compound of Example 109 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 90 parts by weight of the compound of Example 99 is mixed with 10 parts by weight of N-methyl-α-pyrrolidone. A mixture is obtained which is suitable for application in the form of very fine drops.

VI. 20 parts by weight of the compound of Example 109 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VII. 20 parts by weight of the compound of Example 25 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

VIII. 20 parts by weight of the compound of Example 25 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

In these application forms, the agents according to the invention may also be present together with other active ingredients, for example herbicides, insecticides, other growth regulators, and fungicides, and may furthermore be mixed and applied together with fertilizers. Admixture with other growth regulator mixtures gives synergistic effects, i.e., the action of the combination product is greater than the added actions of its components.

USE EXAMPLES

To determine the growth-regulating properties of the candidate compounds, a culture medium was supplied with sufficient nutrients, and test plants were grown therein in plastic pots approx. 12.5 cm in diameter and having a volume of about 500 ml.

In the postemergence treatment, the candidate compounds were applied to the plants as aqueous formulations. The growth-regulating action observed was confirmed at the end of the experiment by measuring the growth height. The figures obtained were compared with those for untreated plants. The commercial growth regulator 2-chloroethyltrimethylammonium chloride (CCC) was used as comparative compound.

Not only was growth height reduced—the leaves also took on a more intense color. The increased chlorophyll content is indicative of a higher rate of photosynthesis, making for bigger yields.

The individual figures are given in the following tables. Separate series of experiments were run with the tosylates (compounds 95 to 114); as a result, different values were obtained for comparative compound A.

EXAMPLE A

Crop: spring barley, "Aramir" variety
Postemergence foliage treatment, concentration: 6 mg of a.i. per vessel

TABLE A

| No. of chem. example | relative growth height (cm) |
|---|---|
| untreated | 100 |
| A | 91.7 |
| 2 | 72.2 |
| 25 | 76.8 |
| 26 | 66.9 |
| 49 | 71.4 |
| 115 | 66.2 |
| 125 | 57.7 |
| 132 | 50.7 |
| 133 | 75.8 |
| 94 | 72.0 |
| tosylates | |
| untreated | 100 |
| A | 90.2 |
| 99 | 79.5 |
| 102 | 82.8 |
| 105 | 83.3 |
| 107 | 69.8 |
| 109 | 52.4 |
| 110 | 69.8 |
| 111 | 70.0 |
| 112 | 77.9 |
| 113 | 76.3 |

EXAMPLE B

Crop: spring wheat, "Kolibri" variety
Postemergence foliage treatment, concentration: 6 mg of a.i. per vessel

TABLE B

| No. of chem. example | relative growth height (cm) |
|---|---|
| untreated | 100 |
| A | 80.2 |
| 99 | 74.6 |
| 107 | 65.1 |
| 110 | 69.8 |
| 111 | 73.0 |

EXAMPLE C

Crop: spring rape, "Petranova" variety

Postemergence foliage treatment, concentration: 6 mg of a.i. per vessel

TABLE C

| No. of chem. example | relative growth height (cm) |
|---|---|
| untreated | 100 |
| A | 91.7 |
| 1 | 83.2 |
| 2 | 80.5 |
| 26 | 68.5 |
| 44 | 84.3 |
| 45 | 86.2 |
| 71 | 83.2 |
| 95 | 70.7 |
| 105 | 78.8 |
| 113 | 76.8 |
| Tosylates untreated | 100 |
| A | 91.6 |
| 95 | 80.3 |
| 102 | 82.4 |
| 107 | 80.3 |
| 109 | 80.7 |
| 110 | 76.2 |
| 111 | 78.2 |
| 112 | 78.2 |
| 113 | 78.2 |

EXAMPLE D

Crop: sunflowers, "Sorex" variety
Postemergence foliage treatment, concentration: 6 mg of a.i. per vessel

TABLE D

| No. of chem. example | relative growth height (cm) |
|---|---|
| untreated | 100 |
| A | 90.6 |
| 1 | 73.2 |
| 19 | 77.5 |
| 25 | 71.6 |
| 26 | 60.4 |
| 44 | 80.0 |
| 45 | 80.0 |
| 77 | 87.4 |
| 95 | 72.7 |
| 112 | 62.0 |
| 121 | 83.5 |
| 94 | 76.2 |
| Tosylates untreated | 100 |
| A | 80.8 |
| 99 | 69.9 |

EXAMPLE E

Crop: rice, "Bahia" variety
Postemergence foliage treatment

TABLE E

| No. of chem. example | Concentration mg per vessel | relative growth height (cm) |
|---|---|---|
| untreated | — | 100 |
| A | 1.5 | 97.5 |
| | 6 | 97.5 |
| 2 | 1.5 | 87.5 |
| | 6 | 75.0 |
| 26 | 1.5 | 95.8 |
| | 6 | 72.8 |
| 49 | 1.5 | 82.5 |
| | 6 | 70.0 |
| Tosylates untreated | — | 100 |
| A | 1.5 | 96.9 |
| | 6 | 96.9 |
| 100 | 1.5 | 87.0 |

TABLE E-continued

| No. of chem. example | Concentration mg per vessel | relative growth height (cm) |
|---|---|---|
| | 6 | 57.1 |

EXAMPLE F

Rice Seedling Test

In further investigations, young rice seedlings (Girona variety) were cultivated in a nutrient solution containing various concentrations of the active ingredients. After six days' growth at 25° C. in continuous light, the active ingredient concentration was determined at which the growth height of the second leaf-sheath is decreased by 50% ($=KI_{50}$).

(Details in W. Rademacher and J. Jung, Berichte aus dem Fachgebiet Herbologie, Issue 24, pp. 127 to 134, University of Hohenheim, 1983).

The results are given in the following table.

TABLE F

| No. of chem. example | $KI_{50}$ (molar) |
|---|---|
| A | $1.5 \times 10^{-2}$ |
| 115 | $6.2 \times 10^{-5}$ |
| 125 | $5.9 \times 10^{-4}$ |
| 132 | $4.4 \times 10^{-5}$ |
| 133 | $5.1 \times 10^{-5}$ |

We claim:

1. A triazole compound of formula Ia or Ib:

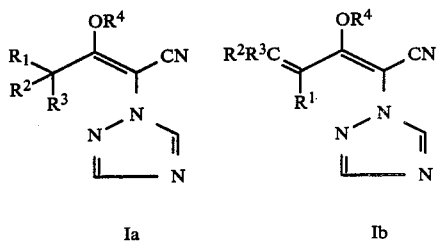

where $R^1$ is hydrogen, cyclopropyl, unsubstituted $C_1$-$C_4$-alkyl or $C_2$-$C_4$-alkynyl, or $C_1$-$C_4$-alkyl, $C_2$-$C_4$-alkenyl or $C_2$-$C_4$-alkynyl substituted by methyl, ethyl, ethenyl, ethynyl, hydroxyl, fluoro, chloro, bromo or $C_1$-$C_4$-alkoxy, or a $C_1$-$C_4$-alkoxy, $C_2$-$C_4$-alkenyloxy or $C_2$-$C_4$-alkynyloxy group, $R^2$ and $R^3$ are identical or different and each denotes hydrogen or straight-chain or branched $C_1$-$C_3$-alkyl, the radicals $R^2$ and $R^3$ may also be a carbocyclic ring, with or without a C1 or C2 alkylene bridge member, with up to six members in each ring system, and with the proviso that, in formula Ia, at least two of radicals $R^1$ to $R^3$ are not hydrogen, and $R^4$ is hydrogen, an acyl radical CO—$R^5$ or a sulfonyl radical SO2—$R^5$, $R^5$ denoting straight-chain or branched $C_1$-$C_8$-alkyl or phenyl optionally substituted by from one to five halogen atoms, $C_1$-$C_4$-alkyl groups, $C_2$-$C_4$-alkenyl groups, $C_1$-$C_4$-alkoxy groups, or cyano groups, or $R^4$ is a metal cation or ammonium.

2. A triazole compound of formula Ia

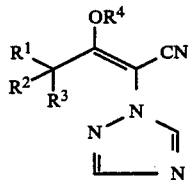 Ia where $R^1$ and $R^2$ are ethyl, $R^3$ is hydrogen or methyl and $R^4$ has the meanings given in claim 1.

3. A process for regulating the growth of plants, wherein the soil, the plants or their seed are treated with an effective amount of a triazole compound of the formulae Ia or Ib, $R^1$ to $R^5$ having the meanings given above.

4. A composition for regulating plant growth, containing an effective amount of triazole compound of the formulae Ia or Ib as set forth in claim 1 and inert additives.

5. A triazole compound of claim 1, wherein, in formula Ia or Ib, said $C_1$–$C_4$ alkyl group of $R^1$ is methyl, ethyl, propyl or butyl and the $C_2$–$C_4$ alkynyl group of $R^1$ is ethynyl, prop-2-ynyl, prop-1-ynyl, but-1-ynyl, but-2-ynyl or but-3-ynyl.

6. The compound of claim 1, wherein said $C_1$–$C_4$-alkoxy group of $R^1$ is methoxy, ethoxy, propoxy, isopropoxy, butoxy, isobutoxy, sec-butoxy or t-butoxy; said $C_2$–$C_4$ alkenyloxy group of $R^1$ is ethenyloxy, prop-2-ynyloxy, prop-1-ynyloxy, but-1-ynyloxy, but-2-ynyloxy or but-3-ynyloxy; and said alkynyloxy group of $R^1$ is ethynyloxy, prop-2-ynyloxy, but-1ynyloxy or but-3-ynyloxy.

7. The compound of claim 1, wherein groups $R^2$ and $R^3$ bonded together form a carbocyclic ring selected from the group consisting of cyclopropyl, cyclobutyl, cyclopentyl and cyclohexyl.

8. The compound of claim 1, wherein said $R^4$ substituent is sodium, potassium or magnesium or an organic amine cation selected from the group consisting of methylammonium, dimethylammonium, trimethylammonium, diisopropylammonium, N-methyldiisopropylammonium, N-ethyldiisopropylammonium, dicyclohexylammonium, piperidinium, N-methylpiperidinium, N,N-dimethylpiperidinium, N-methyl-N-hexylammonium and morpholinium.

9. A triazole compound of the formula:

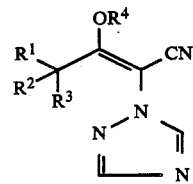

wherein $R^1$, $R^2$ and $R^3$ are each hydrogen or $C_1$–$C_4$-alkyl and $R^4$ is hydrogen.

* * * * *